US008326409B2

(12) United States Patent
Adachi et al.

(10) Patent No.: US 8,326,409 B2
(45) Date of Patent: Dec. 4, 2012

(54) ADJUSTMENT DEVICE, METHOD, AND COMPUTER PROGRAM FOR A BRAINWAVE IDENTIFICATION SYSTEM

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 327 days.

(21) Appl. No.: 12/706,065

(22) Filed: Feb. 16, 2010

(65) Prior Publication Data

US 2010/0145218 A1 Jun. 10, 2010

Related U.S. Application Data

(63) Continuation of application No. PCT/JP2009/001370, filed on Mar. 26, 2009.

(30) Foreign Application Priority Data

Apr. 4, 2008 (JP) ................................. 2008-098339

(51) Int. Cl.
*A61B 5/04* (2006.01)
(52) U.S. Cl. ........................................ 600/545; 600/544
(58) Field of Classification Search .................. 600/544, 600/545
See application file for complete search history.

(56) References Cited

U.S. PATENT DOCUMENTS

| 5,638,826 | A | * | 6/1997 | Wolpaw et al. | 600/544 |
| 5,967,996 | A | * | 10/1999 | Kadota et al. | 600/544 |
| 6,001,065 | A | * | 12/1999 | DeVito | 600/544 |
| 7,945,865 | B2 | * | 5/2011 | Adachi et al. | 715/863 |
| 2001/0056225 | A1 | * | 12/2001 | DeVito | 600/300 |
| 2002/0077534 | A1 | * | 6/2002 | DuRousseau | 600/300 |
| 2004/0097824 | A1 | * | 5/2004 | Kageyama | 600/544 |
| 2005/0008733 | A1 | | 1/2005 | Bae et al. | |
| 2005/0017870 | A1 | * | 1/2005 | Allison et al. | 340/825.19 |
| 2006/0101079 | A1 | * | 5/2006 | Morikawa et al. | 707/104.1 |
| 2009/0142743 | A1 | | 6/2009 | Adachi et al. | |

FOREIGN PATENT DOCUMENTS

JP 08-322269 12/1996
(Continued)

OTHER PUBLICATIONS

International Search Report for corresponding application No. PCT/JP2009/001370 dated Jul. 7, 2009.
(Continued)

*Primary Examiner* — Navin Natnithithadha
*Assistant Examiner* — Etsub Berhanu
(74) *Attorney, Agent, or Firm* — Renner, Otto, Boisselle & Sklar, LLP

(57) ABSTRACT

In a system having an interface which utilizes an electroencephalogram, device operations which are not intended by the user are reduced.
An adjustment apparatus for an electroencephalogram distinction method is used for an electroencephalogram interface system. The system has a biological signal measurement section for acquiring an electroencephalogram signal from a user, and an electroencephalogram interface section for presenting via an output section a plurality of menu items of the manipulation menu in a regular order, distinguishing by a previously determined distinction method a component of an event-related potential which is contained in the electroencephalogram signal after each menu item is highlighted, and operating a device based on the distinguished event-related potential. The adjustment apparatus includes: an analysis section for determining a gradient of a waveform of the event-related potential before the menu item is highlighted; and a determination section for comparing the gradient of the waveform as determined by the analysis section against a threshold value, and determining that the menu item corresponding to the gradient is a menu item which the user wishes to select based on a result of comparison.

9 Claims, 12 Drawing Sheets

FOREIGN PATENT DOCUMENTS

| | | |
|---|---|---|
| JP | 10-146323 | 6/1998 |
| JP | 2005-034620 | 2/2005 |
| WO | 2005/001677 A1 | 1/2005 |
| WO | WO 2007066451 A1 * | 6/2007 |
| WO | 2007/148469 A1 | 12/2007 |

OTHER PUBLICATIONS

Emanuel Donchin et al., "The Mental Prosthesis: Assessing the Speed of a P300-Based Brain-Computer Interface", IEEE Transactions on Rehabilitation Engineering, vol. 8, No. 2, Jun. 2000.

Hiroshi Nittono, "Event-Related Potential Guidebook for Psychology", Kitaoji Shobo, 2005, p. 30-33, and a concise explanation.

Shinichi Niwa, Noriko Tsuru, "Jishokanrendeni, Jishokanrendeni to Shinkeijyohoukagaku No Hatten (or 'Event-Related Potential Event-Related Potential and Developments in Neuroinformation Science')", Shinkoh Igaku Shuppan, 1997, cf. p. 189 and partial English translation.

* cited by examiner

FIG.5
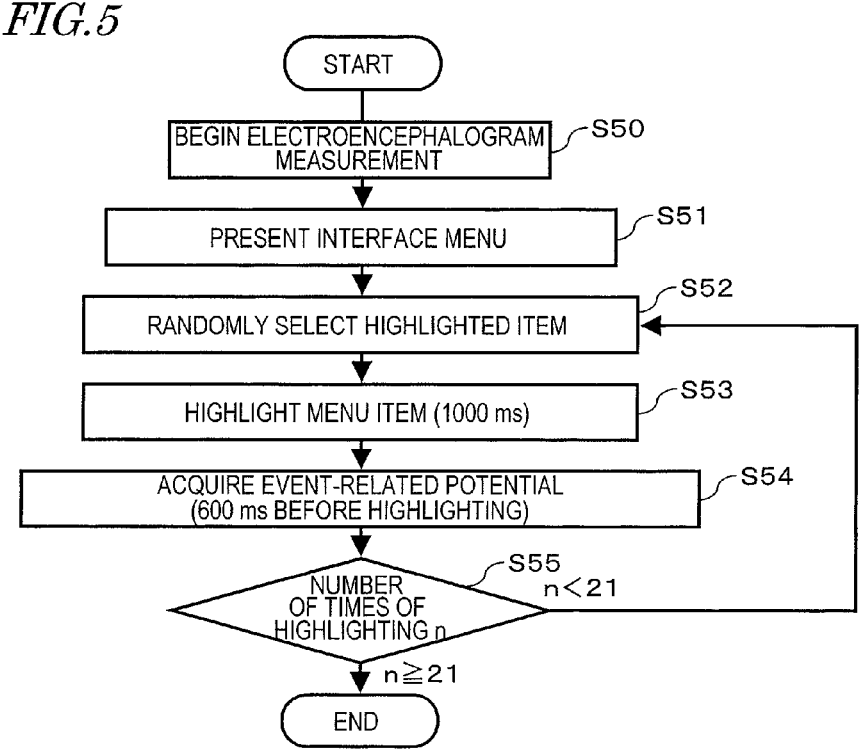
FIG.6
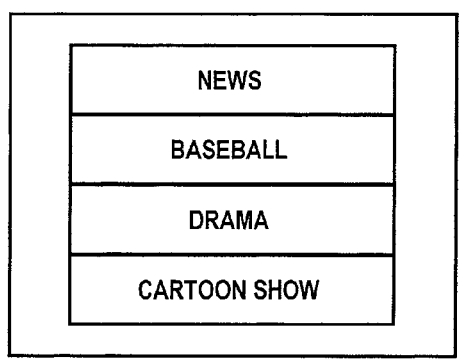
(a) PRESENTED INTERFACE MENU
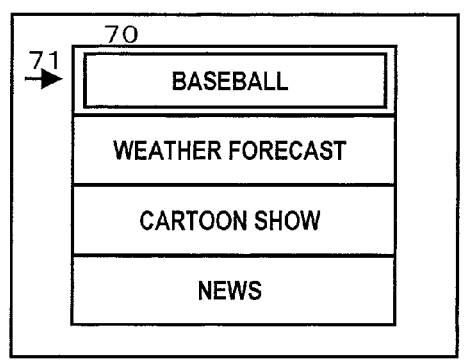
(b) EXAMPLE OF MENU ITEM HIGHLIGHTING (a) SELECTING CONDITION (b) NON-SELECTING CONDITION

ADJUSTMENT DEVICE, METHOD, AND COMPUTER PROGRAM FOR A BRAINWAVE IDENTIFICATION SYSTEM

This is a continuation of International Application No. PCT/JP2009/001370, with an international filing date of Mar. 26, 2009, which claims priority of Japanese Patent Application No. 2008-098339, filed on Apr. 4, 2008, the contents of which are hereby incorporated by reference.

BACKGROUND OF THE INVENTION

1. Field of the Invention

The present invention relates to an interface (electroencephalogram interface) system which allows a device to be manipulated by utilizing an electroencephalogram. More specifically, it relates to an electroencephalogram interface system incorporating an apparatus which, in order to measure and precisely analyze an electroencephalogram of a user in real time, determines whether the user is in a state of issuing an electroencephalogram for selecting a menu item or not by utilizing a negative component of the electroencephalogram of the user while using an electroencephalogram interface, such that the negative component appears before highlighting of a menu item, and eliminates the case where no electroencephalogram for making a selection is being issued.

2. Description of the Related Art

In recent years, various types of information devices such as television sets, mobile phones, PDAs (Personal Digital Assistants) have gained prevalence and entered into people's lives. Thus, users need to manipulate information devices in many scenes of their usual lives. Usually, in realizing a device manipulation, a user utilizes a hand to input an input command via an input means (interface section) such as a button. However, in situations where both hands are full because of tasks other than a device manipulation, e.g. household chores, rearing of children, or driving, it is difficult to make an input by using an interface section and it is impossible to realize a device manipulation. Therefore, there are increasing needs of users to manipulate information devices in every kind of situation.

In answer to such needs, input means utilizing biological signals from a user has been developed. For example, Emanuel Donchin and two others, "The Mental Prosthesis: Assessing the Speed of a P300-Based Brain-Computer Interface", IEEE TRANSACTIONS ON REHABILITATION ENGINEERING, Vol. 8, June 2000 (Hereinafter, Non-Patent Document 1) discloses a electroencephalogram interface that utilizes an event-related potential of an electroencephalogram for distinguishing an option which a user wishes to select. To specifically describe the technique described in Non-Patent Document 1, options are randomly highlighted, and a P3 component of an event-related potential which appears about 300 ms after a point in time that an option was highlighted is utilized to enable distinction of the option which the user wishes to select. According to this technique, a user is able to identify an option which he or she wishes to select, without using a hand.

As used herein, an "event-related potential" refers to a transient potential fluctuation in the brain which occurs in temporal relationship with an external or internal event. An electroencephalogram interface utilizes an event-related potential which is obtained from a stimulation to the visual sense as an external event. For example, within the event-related potential for a visual stimulation, a so-called P3 component may be utilized to perform processing such as switching of channels, selection of a program genre of which viewing is desired, and sound volume level adjustment. The "P3 component" refers to a positive component of the event-related potential which appears in a time slot of 250 ms to 500 ms after a target stimulation is presented, regardless of the type of sensory stimulation such as auditory sense, visual sense, or somatic sensation.

For an application of the event-related potential to an interface, it is important to distinguish the event-related potential (e.g., the P3 component) of a subject with a high accuracy. Therefore, it is necessary to accurately measure a biological signal and accurately distinguish the measured biological signal with an appropriate distinction technique.

There are generally two causes of a lowered distinction ratio. A first cause is that, although being contained in an electroencephalogram, a component (e.g., the P3 component) which is used for an electroencephalogram interface has a low S/N, and results in a low accuracy of the distinction technique. This makes it difficult to perform a highly accurate distinction, and thus the distinction ratio becomes lower. A second cause is that, depending on the state of the test subject, for example, a relevant electroencephalogram component may not have appeared in the first place, thus making it impossible to perform distinction. Since the electroencephalogram interface will try to perform distinction anyway, the electroencephalogram interface will output an incorrect result of distinction. This lowers the distinction ratio.

Regarding the first cause mentioned above, a method for removing the noise mixed in the electroencephalogram and a highly accurate distinction method are both being under development. For example, Pamphlet of International Laid-Open No. 2005/001677 discloses a technique of improving the distinction ratio which uses a band-pass filter to remove, among the noises contained in the electroencephalogram, noises that are mixed at a frequency different from the frequency of a subject of distinction (event-related potential), e.g., noises on commercial power, and thereafter performs distinction. Japanese Laid-Open Patent Publication No. 10-146323 discloses, as a technique of removing noises from living organisms which are difficult to remove with a simple frequency filter, e.g., electro-oculographic potential, a technique of excluding any samples containing an electro-oculographic potential from the subject of distinction, thus obtaining an improved distinction ratio.

Regarding the second cause mentioned above, a technique of excluding any environment which will not allow a relevant electroencephalogram component to appear has been adopted. Specifically, conventional experiments under laboratory room conditions have adopted a technique of controlling the state of a test subject by instructing the test subject to concentrate on a task in a laboratory room which is free of disturbances, or causing the test subject to press a confirmation button, etc., thus allowing a response to steadily appear.

However, when an electroencephalogram interface is used for the manipulation of an actual device that is used on daily basis, e.g., a television set or a DVD recorder, it may not always be the case that the user is concentrating on a screen indication. In other words, an electroencephalogram for making a menu selection may not always appear in the electroencephalogram of the user.

For example, even when a screen of an electroencephalogram interface is being presented, the user may be concurrently performing another task (e.g., household chores or rearing of children), thus resulting in a situation where the user is not looking at the menu but is absorbed in that task. In such a situation, it is difficult to be always gazing at the interface screen. Moreover, if highlighting of a menu item begins while the user is in the process of selecting a menu item to choose next, it results in a situation where no electroencephalogram for making a menu selection is present. The user needs time to select a menu item to choose next. Therefore, it is difficult to assume that an electroencephalogram for making a selection will appear immediately after an electroencephalogram interface menu is presented.

The aforementioned example corresponds to the second cause mentioned above, i.e., a situation where a relevant electroencephalogram component has not appeared in the first place. Since many such situations are conceivable, it is presumable that there will be increasing situations where it is impossible to make an electroencephalogram-based distinction.

Now, when the user is not looking at the menu items, a P3 component will not appear even if a menu item which the user wishes to select is highlighted. However, if a noise of a waveform resembling the P3 component is accidentally mixed, for example, a menu item which is not intended by the user will be selected. This is a problem which is unexpected from any experimentation under laboratory-room conditions, and was first recognized in connection with measuring an electroencephalogram on daily basis for use in an interface.

SUMMARY OF THE INVENTION

An objective of the present invention is to, in a situation where a device is to be manipulated by using an electroencephalogram interface on daily basis, reduce device operations which are not intended by the user.

A adjustment apparatus according to the present invention is: in an electroencephalogram interface system having an output section for visually presenting a manipulation menu for a device, a biological signal measurement section for acquiring an electroencephalogram signal from a user, and an electroencephalogram interface section for presenting via the output section a plurality of menu items of the manipulation menu in a regular order, distinguishing by a previously determined distinction method a component of an event-related potential which is contained in the electroencephalogram signal after each menu item is highlighted, and operating the device based on the distinguished event-related potential, an apparatus used for adjusting the distinction method in the electroencephalogram interface section, wherein the distinction method is a method of distinguishing the component of the event-related potential depending on whether the electroencephalogram signal satisfies a predetermined criterion or not, the adjustment apparatus for the electroencephalogram distinction method comprising: an analysis section for determining a gradient of a waveform of the event-related potential before the menu item is highlighted; and a determination section for comparing the gradient of the waveform as determined by the analysis section against a threshold value, and determining that the menu item corresponding to the gradient is a menu item which the user wishes to select based on a result of comparison.

If the gradient of the waveform determined by the analysis section is smaller than a predetermined negative threshold value, the determination section may determine that the menu item corresponding to the gradient is the menu item which the user wishes to select, and instruct the electroencephalogram interface section to operate the device based on the result of determination.

When determining that the menu item corresponding to the gradient is the menu item which the user wishes to select, the determination section may instruct the electroencephalogram interface section not to perform distinction of the component of the event-related potential which is contained in the electroencephalogram signal after the menu item is highlighted.

The determination section may obtain the gradient of the waveform by dividing the event-related potential ($\mu V$) by time (s), and compare the gradient against the negative threshold value, the negative threshold value being −4.

Wherein, if the gradient of the waveform determined by the analysis section is greater than the predetermined negative threshold value, the determination section may not give any instruction to the electroencephalogram interface section; and the electroencephalogram interface section may distinguish the component of the event-related potential which is contained in the electroencephalogram signal after each menu item is highlighted.

The analysis section may acquire information t representing a time interval of highlighting from the electroencephalogram interface section, and cut out a waveform of the event-related potential from point t2 until point t1, such that point t1 is a point where the menu item is highlighted and point t2 is earlier than point t1 by a predetermined time.

The analysis section may employ a least-squares method to determine the gradient of the waveform of the event-related potential having been cut out.

A adjustment method according to the present invention is: in an electroencephalogram interface system having an output section for visually presenting a manipulation menu for a device, a biological signal measurement section for acquiring an electroencephalogram signal from a user, and an electroencephalogram interface section for presenting via the output section a plurality of menu items of the manipulation menu in a regular order, distinguishing by a previously determined distinction method a component of an event-related potential which is contained in the electroencephalogram signal after each menu item is highlighted, and operating the device based on the distinguished event-related potential, a method used for adjusting the distinction method in the electroencephalogram interface section, wherein the distinction method is a method of distinguishing the component of the event-related potential depending on whether the electroencephalogram signal satisfies a predetermined criterion or not, the adjustment method comprising the steps of: determining a gradient of a waveform of the event-related potential before the menu item is highlighted; and comparing the gradient of the waveform as determined by the step of determining a gradient against a threshold value, and determining that the menu item corresponding to the gradient is a menu item which the user wishes to select based on a result of comparison.

A computer program according to the present invention is: in an electroencephalogram interface system having an output section for visually presenting a manipulation menu for a device, a biological signal measurement section for acquiring an electroencephalogram signal from a user, and an electroencephalogram interface section for presenting via the output section a plurality of menu items of the manipulation menu in a regular order, distinguishing by a previously determined distinction method a component of an event-related potential which is contained in the electroencephalogram signal after each menu item is highlighted, and operating the device based on the distinguished event-related potential, a computer program used for adjusting the distinction method in the electroencephalogram interface section, wherein the distinction method is a method of distinguishing the component of the event-related potential depending on whether the electroencephalogram signal satisfies a predetermined criterion or not, the computer program causing a computer which is provided in the electroencephalogram interface system to execute the steps of: determining a gradient of a waveform of the event-related potential before the menu item is highlighted; and comparing the gradient of the waveform as determined by the step of determining a gradient against a threshold value, and determining that the menu item corresponding to the gradient is a menu item which the user wishes to select based on a result of comparison.

According to the present invention, when a gradient of the waveform of an event-related potential of a user is smaller than a threshold value before highlighting of a menu item, it is possible to determine which menu item the user was wishing to select based on an electroencephalogram (especially event-related potential) before each menu item is highlighted. As a result, rapid processing is expectable, and a reduction in the device operations which are not intended by the user can be realized. Thus, device operations which are not intended by the user due to an erroneous distinction of electroencephalogram are reduced, whereby the manipulability of an electroencephalogram interface can be improved.

Other features, elements, processes, steps, characteristics and advantages of the present invention will become more apparent from the following detailed description of preferred embodiments of the present invention with reference to the attached drawings.

BRIEF DESCRIPTION OF THE DRAWINGS

FIG. 5 A flowchart showing a processing procedure of a device side in a random experiment performed by the inventors.

FIG. 6(a) is a simplified diagram showing menu items which are presented to a test subject, and (b) is a diagram showing an example of highlighting a menu item.

DETAILED DESCRIPTION OF PREFERRED EMBODIMENTS

Hereinafter, with reference to the attached drawings, an embodiment of an electroencephalogram interface system according to the present invention and an adjustment apparatus for a distinction method which is incorporated in the electroencephalogram interface system will be described.

The inventors have found that, when a user is paying attention to a menu item for making a menu selection among highlighted options (menu items), a negative shift appears in an event-related potential of the electroencephalogram before highlighting of the menu item. "negative shift" of an event-related potential refers to a gradual decrease in the value, from positive toward negative, of the event-related potential over time. Typically, it can be detected as a negative gradient of a linear approximation of the waveform of the event-related potential.

According to the present invention, in a system having an interface that utilizes an electroencephalogram, a menu item which a user was wishing to select is determined based on the user electroencephalogram (especially the event-related potential) before highlighting of a menu item. Rapid processing is expectable, and a reduction in the device operations which are not intended by the user can be realized. As a result, without newly adding a gaze detection apparatus or the like, detection of a situation where the user was not issuing an electroencephalogram for selecting a menu item and selection of a menu item can be realized.

Hereinafter, an outline of the electroencephalogram interface system, and experiments which the inventors conducted to ascertain an electroencephalogram component which is characteristic as to whether or not the user is issuing an electroencephalogram for making a menu selection will be first described. Then, the construction and operation of a distinction method adjustment apparatus will be described.

1. Outline of Electroencephalogram Interface System

Figure 1:
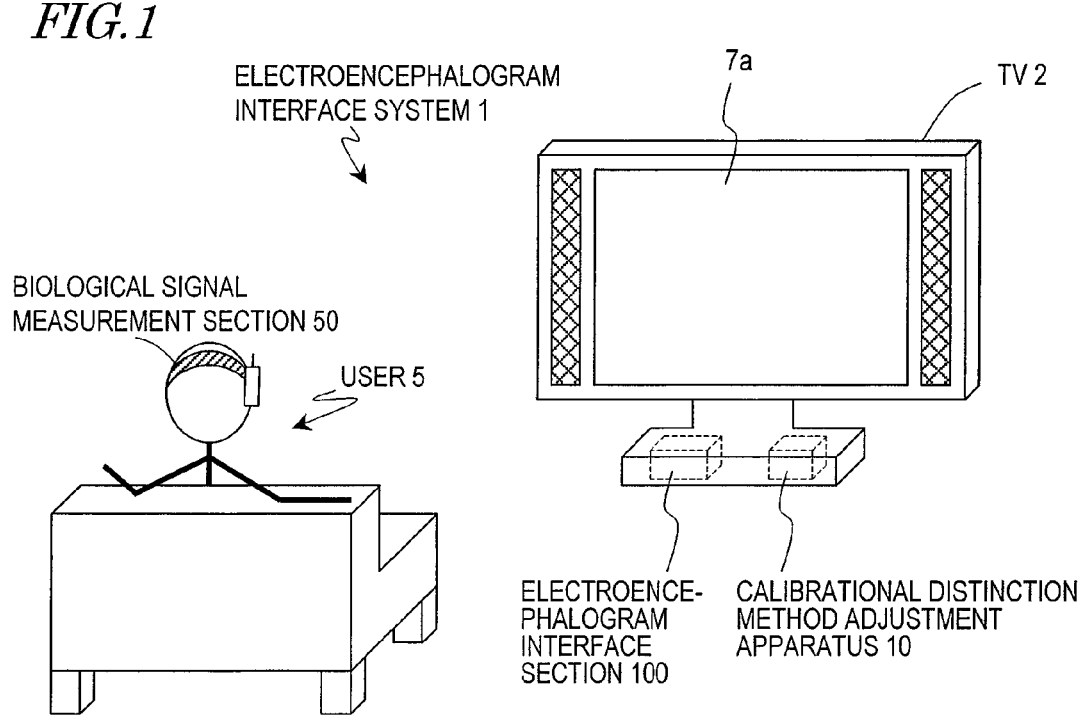
FIG. 1 A diagram showing a construction and an environment of use for an electroencephalogram interface system 1.

FIG. 1 illustrates a construction and an environment of use for the electroencephalogram interface system 1. The electroencephalogram interface system 1 is exemplified so as to correspond to a system construction of an embodiment of the present invention described later.

The electroencephalogram interface system 1 is a system for providing an interface for manipulating a TV 2 by utilizing an electroencephalogram signal from a user 5. An electroencephalogram signal from the user 5 is acquired by a biological signal measurement section 50 which is worn on the head of the user, and transmitted to an electroencephalogram interface section 100 in a wireless or wired manner. The electroencephalogram interface section 100 internalized in the TV 2 recognizes an intent of the user by utilizing a component called an event-related potential, which constitutes a part of the electroencephalogram, and performs processes such as switching of channels.

Figure 2:
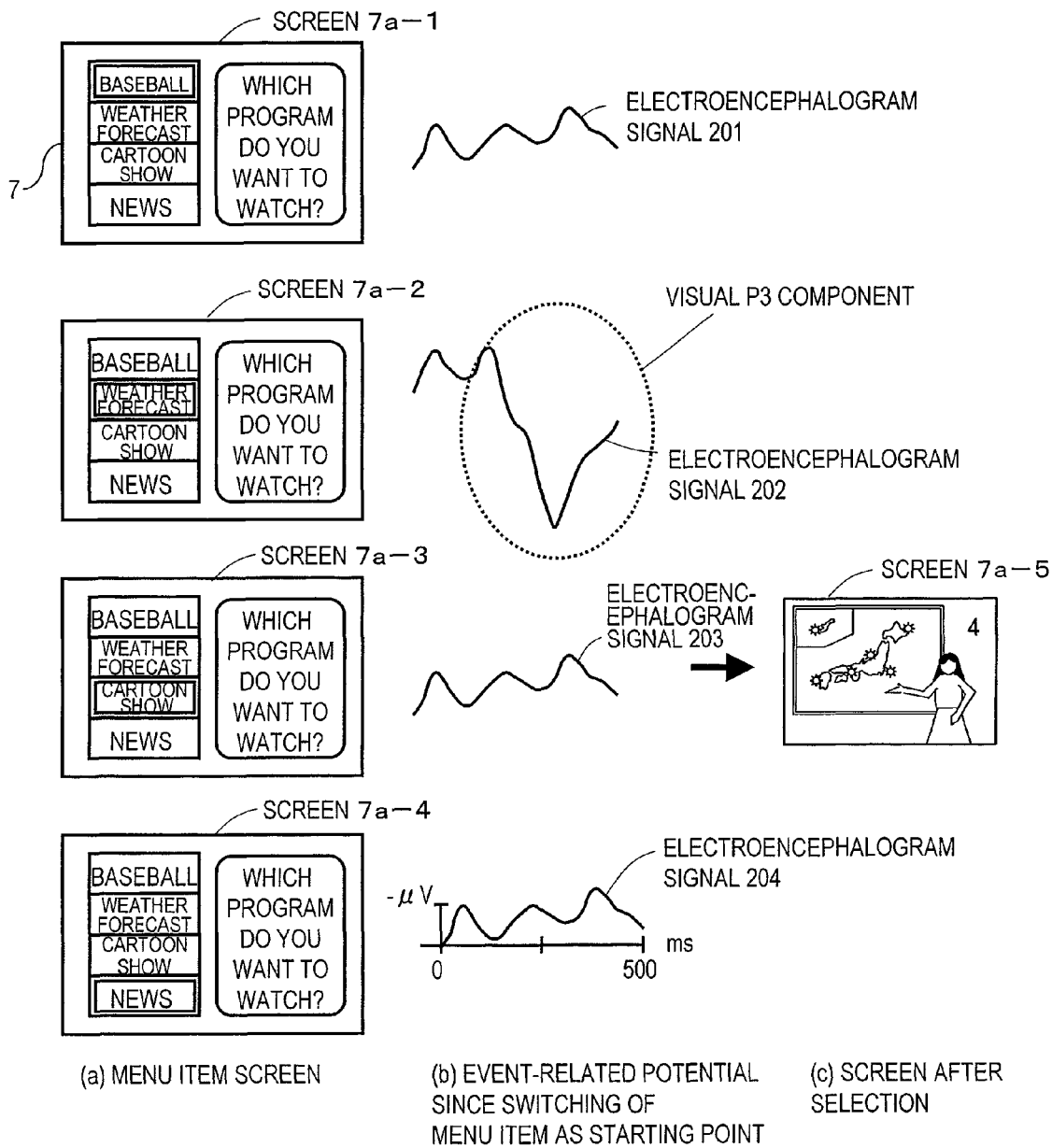
FIG. 2(a) to (c) are diagrams showing an example where a TV 2 is manipulated in the electroencephalogram interface system 1 and a user 5 watches a program of a genre which he or she wishes to view.

FIG. 2 shows an example where the TV 2 is manipulated in the electroencephalogram interface system 1 and the user 5 watches a program which he or she wishes to view.

FIG. 2(a) is an exemplary menu which the electroencephalogram interface section 100 presents to the user via a screen 7a of the TV 2. In FIG. 2(a), a screen 7a-1 to a screen 7a-4 respectively illustrate how menu items "baseball", "weather forecast", "cartoon show", and "news" are highlighted in order or at random. In the present specification, the group of options concerning device manipulations as shown in FIG. 2(a) is defined as a "menu", whereas each option is defined as a "menu item". By highlighting menu items, it becomes possible to measure the event-related potential since a point of highlighting each menu item as a starting point. Note that, a menu may be presented by a pointer using an auxiliary arrow 71 instead of highlighting, or in addition to a highlight 70 as shown in FIG. 6(b) described later.

FIG. 2(b) schematically shows the event-related potential of an electroencephalogram signal from the user which is measured since a point of highlighting a menu item as a starting point. It is assumed that the user is currently wishing to watch "weather forecast". Among electroencephalogram signals 201 to 204 respectively corresponding to the screen 7a-1 to the screen 7a-4, if the user 5 looks at the screen 7a-2 in which "weather forecast" is highlighted, a characteristic positive component appears with a latent period of about 400-450 ms since the point of highlighting "weather forecast" as a starting point (Non-Patent Document 1).

When the electroencephalogram interface section 100 distinguishes this appearance of the P3 component, selection of the menu item "weather forecast" which the user wishes to select becomes possible. FIG. 2(c) shows the screen 7a-5, which comes after the channel has been switched to "weather forecast" as a result of distinguishing the P3 component.

Figure 3:
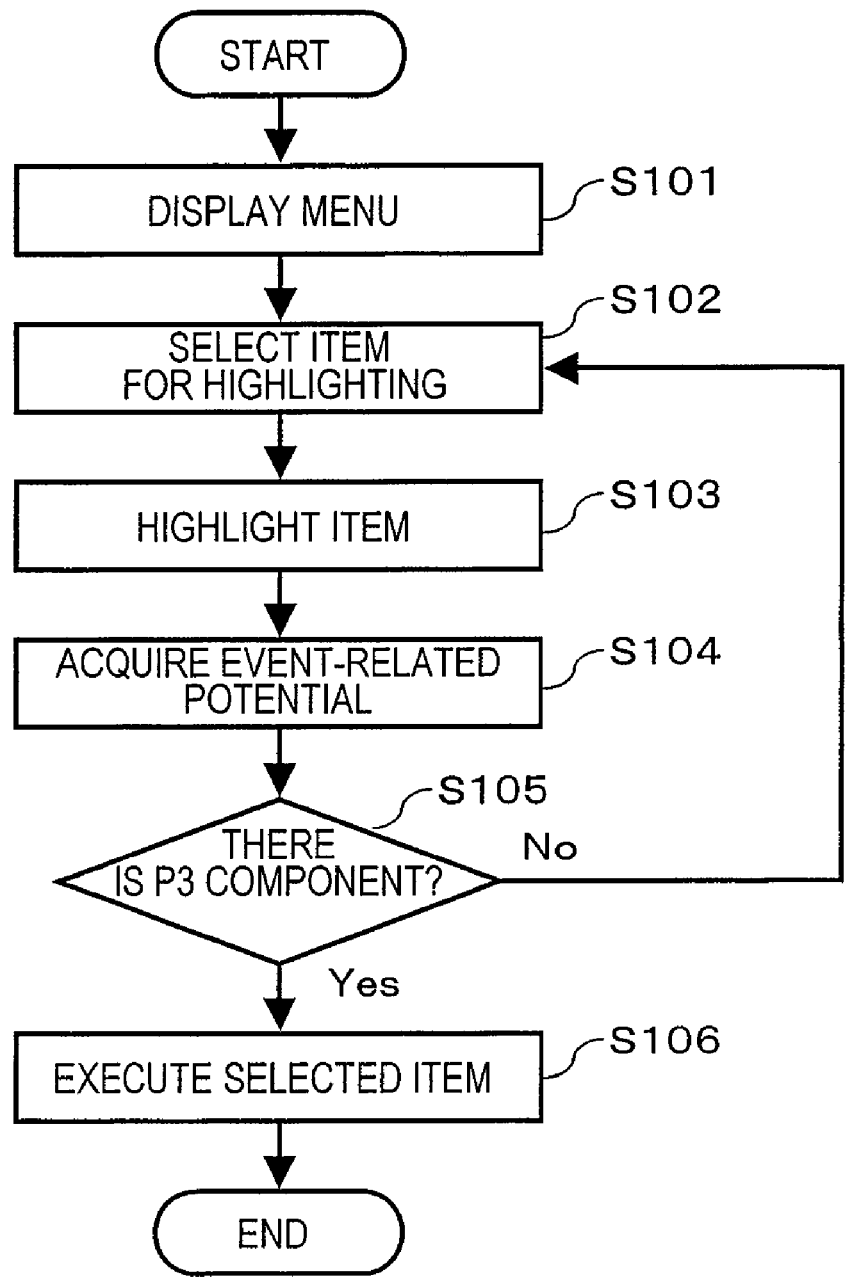
FIG. 3 A flowchart showing an exemplary processing procedure A of an electroencephalogram interface.

FIG. 3 shows an exemplary processing procedure of an electroencephalogram interface (processing procedure A). At step S101, the electroencephalogram interface section 100 presents an electroencephalogram interface menu containing e.g. four menu items (the left-hand side of FIG. 2(a)). At this point, although not essential, an inquiring sentence (the right-hand side of FIG. 2(a)) may be presented together with the electroencephalogram interface menu. At step S102, the electroencephalogram interface section 100 selects a menu item to be next highlighted. The menu item to be next highlighted may be selected in random order, or in descending order. At step S103, the menu item selected at step S102 is highlighted.

At step S104, the electroencephalogram interface section 100 measures the event-related potential of the user for the duration of e.g. 500 ms since the point of highlighting a menu item at step S103 as a starting point. The zone to be cut out as the event-related potential may be e.g. 800 ms, 1000 ms, so long as the P3 component appearing at 300-500 ms is contained therein. Herein, event-related potentials 201 to 204 of the electroencephalogram signals schematically shown in FIG. 2(b) are measured.

At step S105, distinction is made as to whether the P3 component is contained in the event-related potential measured at step S104 or not. Distinction of the P3 component may be made by simply determining whether the maximum amplitude of the waveform or an average potential of a given zone of the waveform is greater than a threshold value which is previously set, or as described in Japanese Laid-Open Patent Publication No. 10-146323, a correlation coefficient may be determined with respect to a template which is generated from an arithmetic mean waveform of the P3 component that has been measured with respect to each user in advance. Note that a threshold value may be determined with respect to each user. If Yes at step S105, control proceeds to step S106; if No, control returns to step S102 and the next menu item is selected.

At step S106, the electroencephalogram interface section 100 executes a process corresponding to the menu item selected at step S105. As a result, that menu item is selected and executed, whereby the screen 7a-5 shown in FIG. 2(c) is displayed. For example, in the example of FIG. 2, weather forecast is selected, and the weather forecast program is being presented.

In accordance with the electroencephalogram interface system 1 as such, the user is able to manipulate a device such as the TV 2 without using a hand, even in the case where their both hands are full due to a household chore or rearing of children, for example. Thus, the manipulability of the device is significantly improved.

In the above-described process, if the user is not issuing an electroencephalogram for making a selection because of not looking at the menu or being in the process of choosing a menu item to be selected at the timing when a menu item is highlighted, the P3 component is not measured at step S103. However, if a noise (e.g. electro-oculographic potential) mixes into the event-related potential acquired at step S104 and exhibits a waveform resembling the P3 component, there is a possibility that step S105 may determine that the P3 component exists and that a menu item not intended by the user may be selected at step S106.

As another distinction method, a procedure of processing (processing procedure B described later) of comparing the event-related potentials after the respective menu items are highlighted and selecting one that possesses the highest possibility that the P3 component has appeared may be used; however, there is a similar possibility that a menu item not intended by the user may be selected. When processing procedure B is employed, it is possible to select what is close to the P3 component based on comparison of event-related potentials, thus making it possible to realize a device operation even when some noise is mixed.

Figure 4:
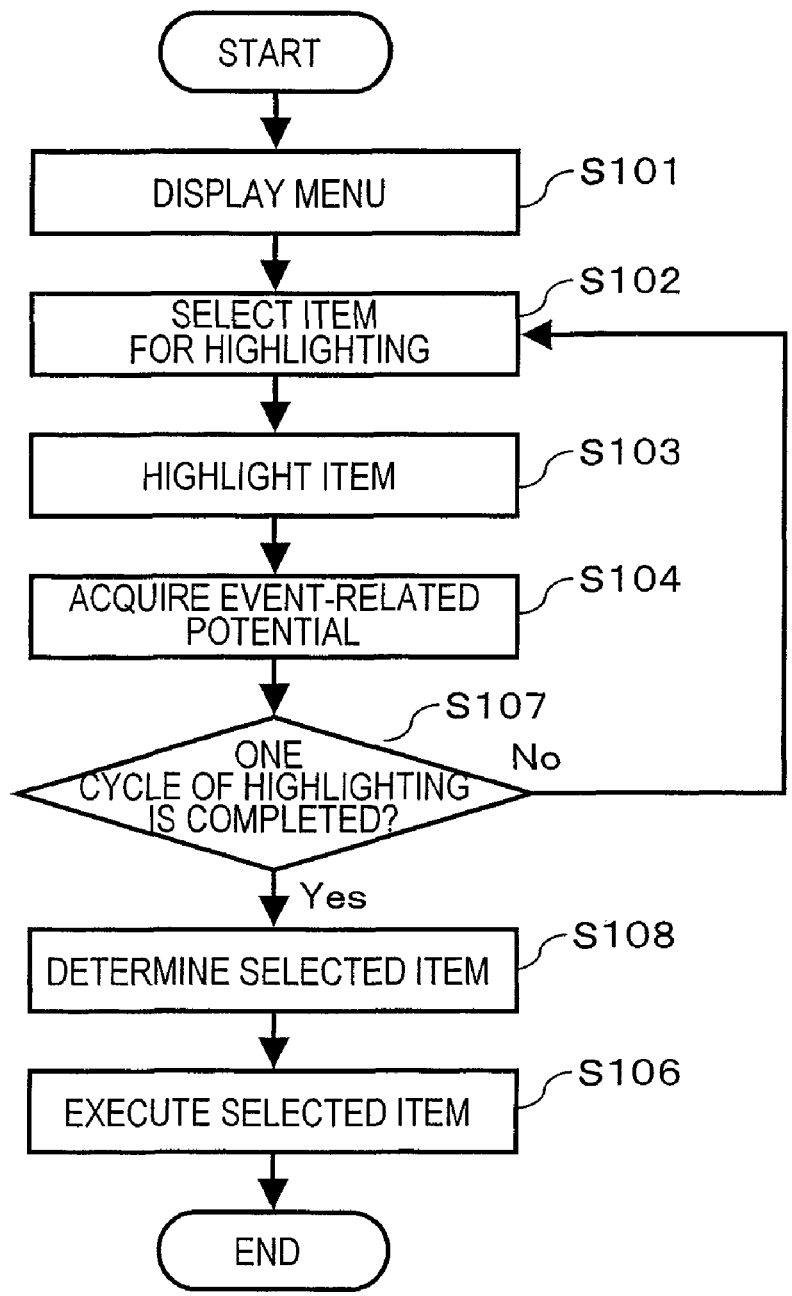
FIG. 4 A flowchart showing an exemplary processing procedure B of an electroencephalogram interface.

FIG. 4 shows processing procedure B of an electroencephalogram interface. Note that any step where the same process as in processing procedure of the electroencephalogram interface shown in FIG. 3 is performed is denoted by the same numeral, and the description thereof is omitted. Step S107 branches out depending on whether or not every selected item has been highlighted at least once. If Yes at step S107, control proceeds to step S108; if No, control returns to step S102, and the next menu item is selected.

At step S108, a possibility that the P3 component is contained in the event-related potential of each menu item acquired at step S104 is calculated; an item-by-item comparison is made; and the closest menu item is distinguished as containing the P3 component and determined to be the selected item. The calculation of the possibility that the P3 component is contained in the event-related potential of each item may be made by simply selecting the waveform whose maximum amplitude value is the largest as in step S104 in FIG. 3, or by determining the size of an average potential in a given zone and selecting one that has the largest average potential. Alternatively, it may be made by selecting one that has a large correlation coefficient value with respect to a template.

Thus, by comparing the event-related potential of each menu item and choosing the selected item having the highest possibility that the P3 component has appeared, a distinction method is realized that enables distinction even if some noise is mixed. This is similarly true when processing procedure B is employed. However, even if the user is not issuing an electroencephalogram for making a selection because of not looking at the menu or being in the process of choosing a menu item to be selected, a menu item will also be selected because the event-related potential in connection with the menu item is mistakenly regarded as containing the P3 component. Therefore, there is a possibility that a menu item not intended by the user may be selected.

Selection of such a menu item not intended by the user occurs all because the device is unable to determine whether the user was issuing an electroencephalogram for making a menu selection or not. If it is possible to determine whether he or she was issuing an electroencephalogram for making a menu selection or not, such unintended device operations can be eliminated by adjusting the distinction method, e.g., by excluding from the subject of distinction the case of not issuing an electroencephalogram for making a menu selection.

The inventors have found that, by determining whether or not the electroencephalogram of a user who uses an electroencephalogram interface had a negative shift before highlighting of a menu item, it is possible to determine whether the user is issuing an electroencephalogram for making a menu selection or not. As a result, without newly adding a gaze detection apparatus or the like, a detection that the user was not issuing an electroencephalogram for making a menu selection can be realized. Hereinafter, experiments performed by the inventors and the experimental results thereof will be described with reference to FIG. 5 to FIG. 11.

2. Experiment

By changing the method of highlighting, two participants (male) were subjected to two types of experiments: a random experiment where menu items were highlighted in random order; and a descending-order experiment where highlighting was performed in descending order. The electroencephalogram was measured from Pz on the scalp (International 10-20 system) relative to the right earlobe. Moreover, visual stimulations were presented on a 37" plasma display which was placed 2 m in front of the test subjects.

First, the random experiment will be described. In the random experiment, in order to examine differences in waveform depending on whether the user was issuing an electroencephalogram for making a selection or not, an experiment was performed under the two conditions of a condition of issuing an electroencephalogram for making a menu selection and a condition of not issuing an electroencephalogram for making a menu selection, and the waveforms before highlighting of menu items were compared.

Firstly, with reference to FIG. 5, a flow of the device side of the random experiment will be described. The flow of the device side is similar irrespective of the conditions of issuing or not-issuing an electroencephalogram for making a menu selection.

Step S50 is a step of beginning electroencephalogram measurement for a test subject.

Step S51 is a step of presenting four menu items of an electroencephalogram interface menu, thus indicating to the user what kinds of menu items there are. FIG. 6(*a*) shows simplified the menu items which were actually presented to the test subjects. In our experiment, presentation of four menu items was made for 2 seconds. Note that step S51 also has an effect of stabilizing the electroencephalogram before highlighting of a menu item and reducing noises such as an electro-oculographic potential.

Step S52 is a step of randomly selecting a menu item to be next highlighted. It was ensured that no same menu item was successively selected.

Step S53 is a step of highlighting the menu item selected at step S52 for 1000 ms. An example of highlighting is shown in FIG. 6(*b*).

Step S54 is a step of cutting out an electroencephalogram before the highlighting, based on the point of highlighting the menu item at step S53 as 0 ms, and acquiring an event-related potential. The event-related potential which was cut out spanned 600 ms, from 600 ms before the highlighting (where there would be little influence from an immediately previous highlight) until the highlighting was made.

Step S55 is a branching based on the number n of times that the menu items have been highlighted, where control proceeds to step S52 to repeat highlighting of menu items if the number of times of highlighting is smaller than 21. As a result of this, highlighting is performed five times for each menu item (20 times÷4 menu items). This is a step of experimentally taking a repetitive arithmetic mean of event-related potentials for enabling a surer confirmation of components. Note that step S55 does not need to be performed in actual use of an electroencephalogram interface.

Through step S50 to step S55 above, 20 samples of event-related potentials based on highlighting as a starting point can be recorded when each menu item is highlighted about 5 times.

Next, a flow of the participant side of the random experiment will be described with reference to FIG. 7.

Figure 7:
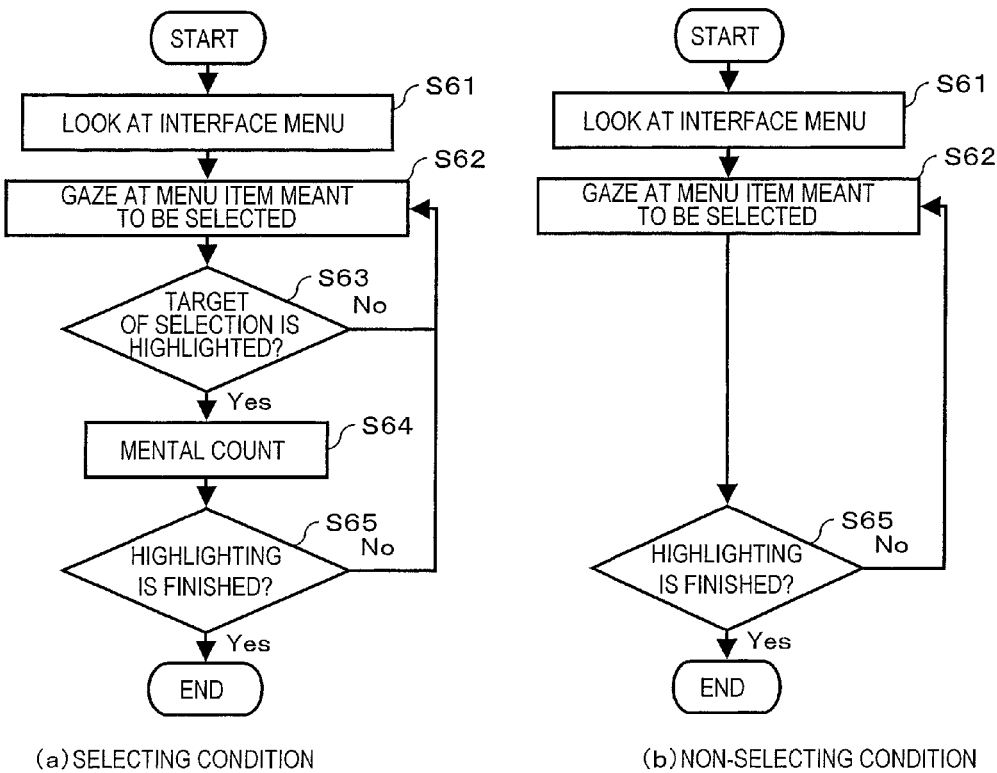
FIGS. 7(a) and (b) are flowcharts of a participant side in a random experiment performed by the inventors.

FIG. 7(*a*) is a diagram showing a flow of the participant side under the condition of issuing an electroencephalogram for making a menu selection (selecting condition).

Step S61 is a step of looking at the menu presented at step S51 in FIG. 5. The test subject is instructed in advance to select a menu item in order from top to bottom, and moves his or her gaze to a menu item meant to be selected. The instruction of an item meant to be selected corresponds to a device operation which a user wants to realize when the user actually uses an electroencephalogram interface.

Step S62 is a state of gazing at the menu item meant to be selected, and while looking at the menu items presented at steps S52 to S55 in FIG. 5(*a*) being highlighted, waiting for the menu item meant to be selected to become highlighted.

Step S63 is a branching based on whether the menu item meant to be selected has been highlighted at step S62 or not. If Yes at step S63, control proceeds to step S64; if No, control proceeds to step S62.

Step S64 is a step of taking a mental count of the number of times that the menu item meant to be selected has been highlighted at step S62. A mental count means counting out numbers in mind. This is known to induce a P3 component in the event-related potential.

Step S65 is a branching based on whether a predetermined number of times of highlighting has been finished or not. If Yes at step S65, control proceeds to END; if No, control proceeds to step S62.

FIG. 7(*b*) is a diagram showing a flow of the participant side under the condition of not issuing an electroencephalogram for making a menu selection (non-selecting condition). Steps at which the same processes as those under the selecting condition shown in FIG. 7(*a*) are performed will be denoted by like reference numerals, and the descriptions thereof will be omitted.

The difference from the selecting condition is that step S63 and step S64 for issuing an electroencephalogram for making a menu selection are eliminated. As a result, the participant is in a state of just looking at the highlighted menu items without an intent of making a selection.

Figure 8:
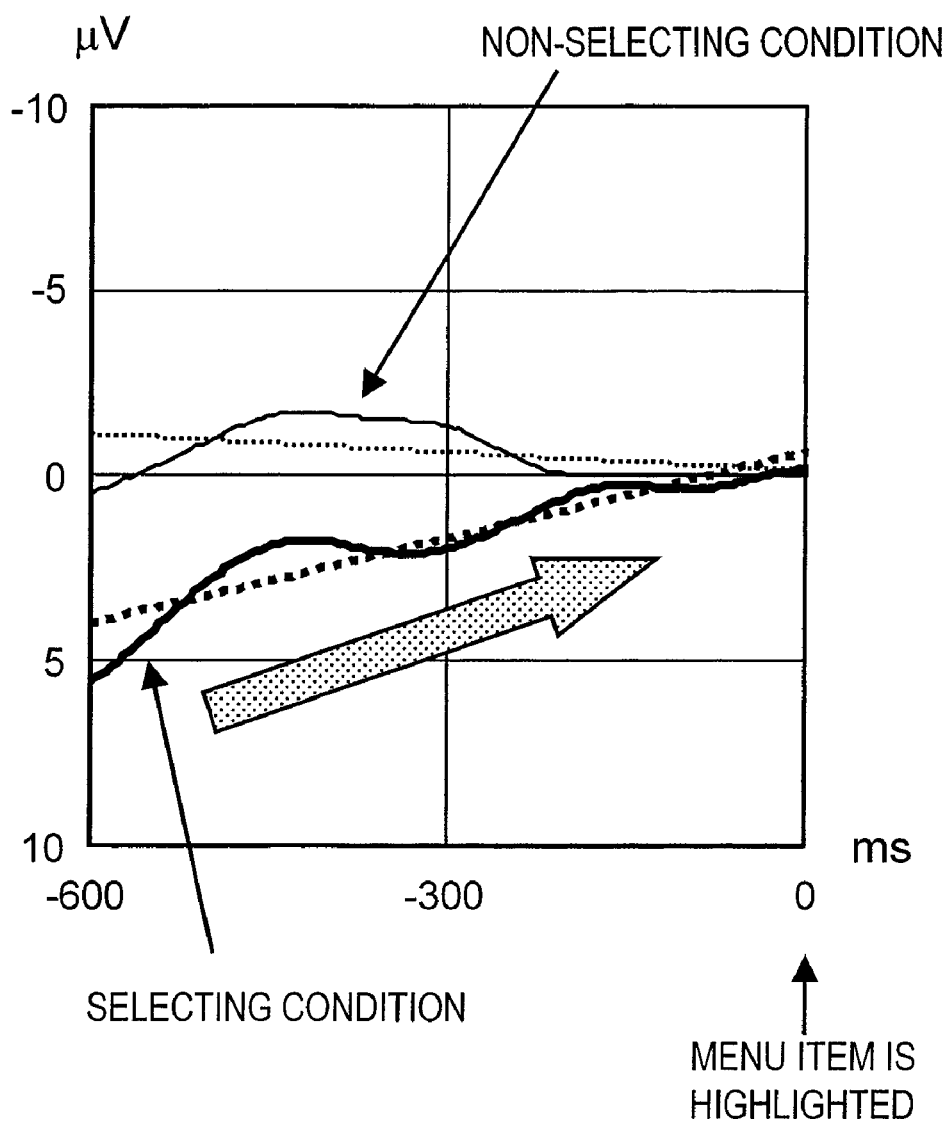
FIG. 8 A graph showing total arithmetic mean waveforms of an event-related potential at 600 ms before highlighting.

Exemplary experimental results are shown in FIG. 8. FIG. 8 shows total arithmetic mean waveforms of the event-related potential at 600 ms before highlighting. Since the event-related potential to be analyzed is in a zone before highlighting, an arithmetic mean of the event-related potential before every highlight was taken, irrespective of whether the highlight was directed to the item meant to be selected or not. A baseline correction was performed based on an average potential at 50 ms before highlighting, and any sample the maximum value of whose amplitude exceeded 100 µV was excluded from the subject of distinction, because of possibly containing noises such as the electro-oculographic potential. FIG. 8 shows a total arithmetic mean waveform under the selecting condition and a total arithmetic mean waveform under the non-selecting condition, with a thick solid line and a thin solid line, respectively. The horizontal axis represents time in units of ms, whereas the vertical axis represents potential in units of µV. Under the selecting condition, the waveform was shifted in the negative direction toward 0 ms (beginning of next highlight). However, under the non-selecting condition, no negative shift was observed. By using a least-squares method, the gradients of the total arithmetic mean waveforms were determined to be −7.74 μV/s and 1.65 μV/s under the selecting condition and the non-selecting condition. The gradients are shown in FIG. 8 with a thick dotted line and a thin dotted line, respectively.

This negative shift is considered as a component which appears only under the selecting condition, as a reflection of a stand-by state for a next highlight. Therefore, in an electroencephalogram interface where menu items are randomly highlighted, it can be determined whether the user was issuing an electroencephalogram for making a menu selection or not on the basis of the presence or absence of a negative shift before highlighting. The determination of the presence or absence of a negative shift can be easily made based on the sign of the determined gradient, which is synonymous with comparing the determined gradient against a threshold value which is a 0 gradient.

It is generally known that a contingent negative potential called the CNV (Contingent Negative Variation) appears as a negative shift which reflects a stand-by state for a stimulation. The CNV component is a mild negative potential which is recorded in a state of waiting for an imperative stimulus after a preliminary stimulus, and is supposed to be strongly related to psychological factors such as anticipation, attention, volition, motivation, and the like (see for example, Shinichi NIWA, Noriko TSURU: "JISHOKANRENDENI JISHOKANRENDENI TO SHINKEIJYOHOUKAGAKU NO HATTEN (or 'event-related potential event-related potential and developments in neuroinformation science')", Shinkoh Igaku Shuppan, 1997, cf. P189). However, it has not been known that differences exist in the negative shift amount in connection with whether a user was issuing an electroencephalogram for making a menu selection upon use of an electroencephalogram interface.

Next, the descending-order experiment will be described. Unlike in the random experiment, in the descending-order experiment where menu items are highlighted in descending order, the user is able to infer a menu item to be next highlighted and does not need to cautiously await every highlight in order to determine whether it was meant to be selected or not. Therefore, the descending-order experiment is performed under the condition where the user would issue an electroencephalogram for making a menu selection, thus examining the influences on the negative shift that are exerted by different dispositions regarding highlights. It also examines whether a menu item meant to be selected can be determined based on an electroencephalogram before highlighting.

Figure 9:
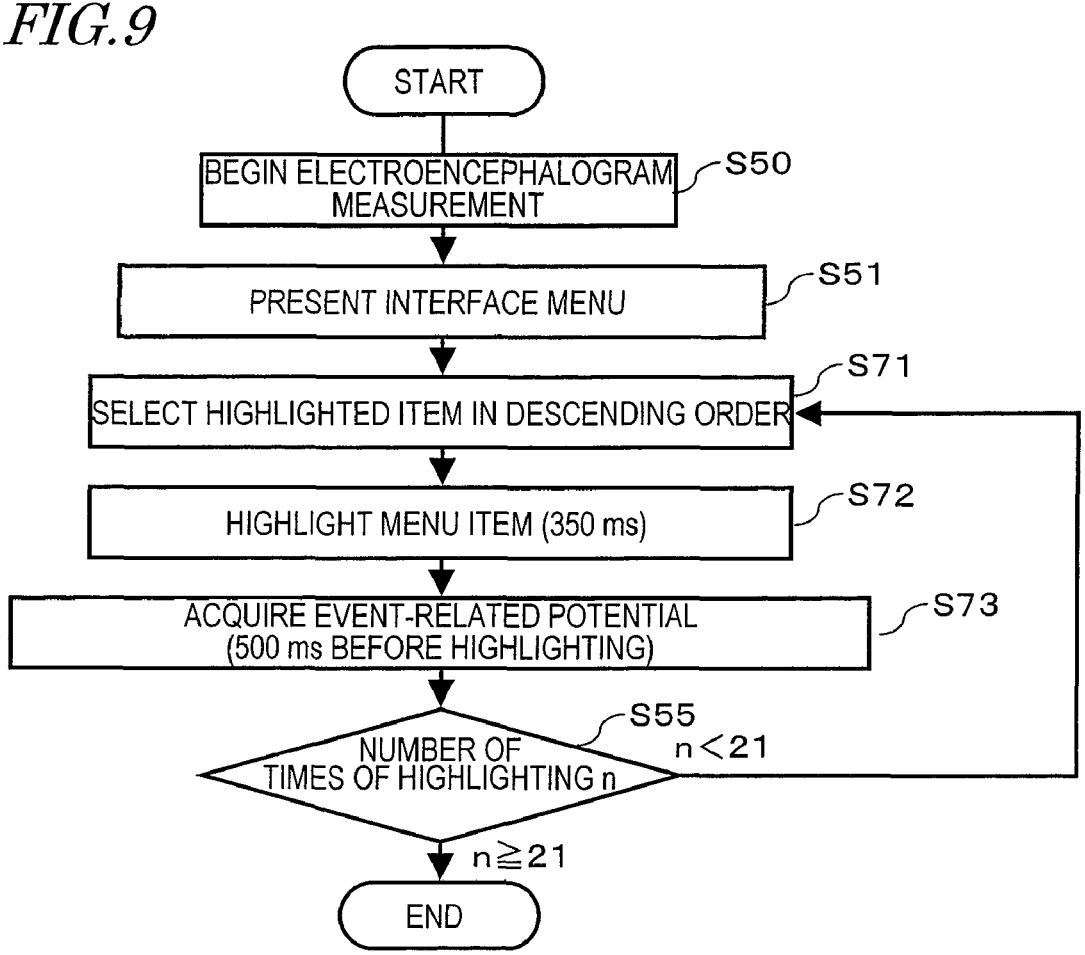
FIG. 9 A processing flow of a device side in a descending-order experiment performed by the inventors.

First, a flow of the device side of the descending-order experiment will be described with reference to FIG. 9. Steps at which the same processes as those in the random experiment illustrated in FIG. 5 are performed will be denoted by like reference numerals, and the descriptions thereof will be omitted.

The difference from the random experiment is that the menu items are highlighted in descending order, for 350 ms each.

Step S71 is a step of selecting a menu item to be next highlighted in descending order.

Step S72 is a step of highlighting the menu item selected at step S71 for 350 ms.

Step S73 is a step of cutting out 500 ms of electroencephalogram, from 500 ms before the highlighting until the highlight was made, based on the point of highlighting the menu item at step S72 as 0 ms, and acquiring the event-related potential.

Next, a flow of the participant side of the descending-order experiment will be described with reference to FIG. 10.

Figure 10:
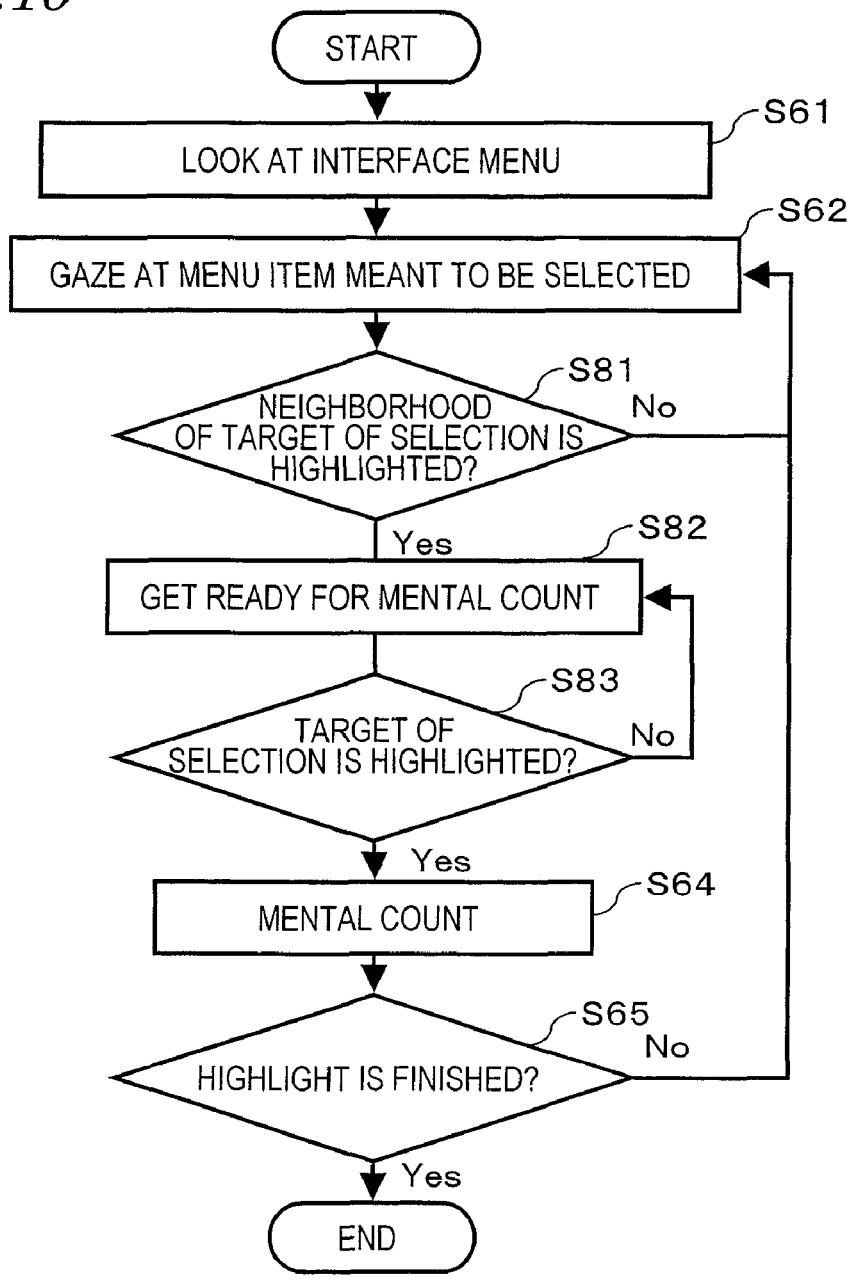
FIG. 10 A processing flow of a participant side in a descending-order experiment performed by the inventors.

FIG. 10 is a diagram showing a flow of the participant side the descending-order experiment. Steps at which the same processes as those of the flow of the participant side in the random experiment illustrated in FIG. 7 are performed will be denoted by like reference numerals, and the descriptions thereof will be omitted. The descending-order experiment was performed under the selecting condition where the participant would issue an electroencephalogram for making a menu selection.

The difference from the flow of the participant side of the random experiment shown in FIG. 7 is that, since a menu item to be next highlighted can be inferred in the descending-order experiment, the determination as to whether each highlight was directed to a menu item meant to be selected or not, as in the random experiment (step S63 of FIG. 7(*a*)), is not made.

In the descending-order experiment, the participant is able to infer the timing as to when the menu item meant to be selected will be highlighted. Therefore, it is presumable that the preparation for highlight detection and detection of a highlight of the menu item meant to be selected are made only in the neighborhood of the inferred timing.

Step S81 is a branching based on whether one or two menu items (plural number) before the menu item meant to be selected was highlighted or not. If Yes at step S81, control proceeds to step S82; if No, control proceeds to step S62.

Step S82 is a step of getting ready to take a mental count, responsive to one or two menu items (plural number) before the menu item meant to be selected becoming highlighted at step S81.

Step S83 is a branching as to detecting the highlighting of a menu item meant to be selected. If Yes at step S83, control proceeds to step S64; if No, control proceeds to step S82.

Figure 11:
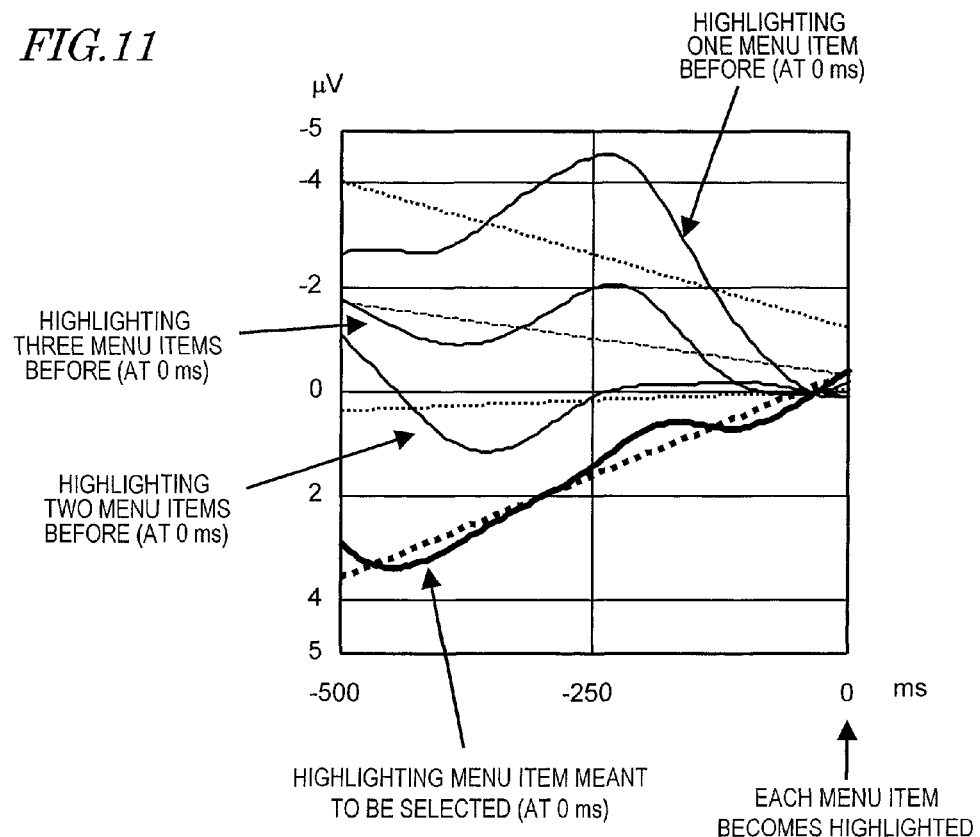
FIG. 11 A diagram showing arithmetic mean waveforms indicative of results of a descending-order experiment.

Exemplary experimental results are shown in FIG. 11.

FIG. 11 shows waveforms obtained by taking total arithmetic means (2 people) of 500 ms of event-related potential, from 500 ms before the highlighting of each menu item until the highlighting is made, based on how many menu items there were before the menu item meant to be selected. Note that a baseline correction was performed based on an average potential at 50 ms before highlighting, and any sample the maximum value of whose amplitude exceeded 100 μV was excluded from the subject of distinction because of possibly containing noises such as the electro-oculographic potential. FIG. 11 shows a total arithmetic mean waveform of the case where the menu item meant to be selected was highlighted at 0 ms (hereinafter, waveform 0) with a thick solid line, and shows total arithmetic mean waveforms of the cases where one, two, or three menu items before the item meant to be selected was highlighted (hereinafter, waveform 1, waveform 2, waveform 3) with thin solid lines. From FIG. 11, it can be seen that the total arithmetic mean waveform before the menu item meant to be selected is highlighted at 0 ms (waveform 0) has a relatively great shift in the negative direction, whereas the other waveforms 1 to 3 have substantially no shift in the negative direction. By using the least-squares method, the gradient of each total arithmetic mean waveform was determined as follows: the gradient of waveform 0 was −7.85 μV/s; and the gradients of waveform 1 to waveform 3 were 5.56 μV/s, −0.78 μV/s, and 2.82 μV/s, respectively. The gradients are also shown in FIG. 11. As a threshold value of gradient for distinguishing waveform 0 from waveforms 1 to 3, −4 or −5 (μV/s) can be adopted, for example.

Presumably, the negative shift appearing in waveform 0 reflects a stand-by state for highlighting of the menu item meant to be selected, in the case where highlighting is performed under a setting where the highlighting of a menu item is inferable, as in the descending-order experiment. Moreover, no negative shift appears when anything other than the menu item meant to be selected is highlighted. Thus it can be said that, under a setting where the highlighting of a menu item is inferable, it is possible to determine which menu item the user selected before highlighting of a menu item, based on whether an event-related potential before highlighting of a menu item was shifted in the negative direction or not. Moreover, in the case where highlighting is performed under a setting where the highlighting of a menu item is inferable, the user may be determined as issuing an electroencephalogram for making a selection if the waveform has a negative shift before highlighting of at least one menu item.

Hereinafter, a distinction method adjustment apparatus according to the present invention and an electroencephalogram interface system including the adjustment apparatus will be described.

Generally speaking, when stimulations are presented in a regular order such as descending order, it is said that the P3 component will have a smaller amplitude because the timing for the user to respond (when the menu item which he or she wishes to select is highlighted) is predictable, thus making it difficult to distinguish the P3 component. Therefore, in any electroencephalogram interface whose distinction accuracy is deemed important, it has often been the case to perform highlighting in random order, and a highlight setting in descending order has not been preferred.

However, from the standpoint of the user's burden concerning selection, less burden is incurred by highlighting in descending order, where response is to be made only at the predicted highlight timing, than by random highlighting, where every highlight needs to be subjected to a determination as to whether it was meant to be selected or not. Against this background, in a user electroencephalogram when a plurality of menu items are highlighted in descending order, the distinction method adjustment apparatus according to the present invention determines gradients of event-related potentials before highlighting of menu items, and based on the determined gradients, determines whether the user was issuing an electroencephalogram for making a menu selection or not, and further determines which gradient has a negative shift or not. Thus, if the user is not issuing an electroencephalogram for making a menu selection, it is excluded from the subject of distinction, thus making it possible to reduce device operations which are not intended by the user; and when the user is issuing an electroencephalogram for making a menu selection, it is possible to identify which menu item the user is wishing to select.

3. Embodiment of the Electroencephalogram Interface System According to the Present Invention The results of the aforementioned descending-order experiment indicate that, in the case where menu items are highlighted in descending order, the determination of a menu item that the user has selected can be made based only on negative shift amount(s) before highlighting of the menu item(s).

Based on these results, in the electroencephalogram interface system according to the present embodiment, menu items are highlighted in descending order, and a gradient (negative shift amount) of an event-related potential before highlighting is determined for each highlight, and a menu item meant to be selected is determined based only on the negative shift amounts. Thus, by performing a determination with the negative shift amount of an event-related potential before highlighting as an index, it is possible to determine a menu item meant to be selected immediately before highlighting, thus making it unnecessary to observe a waiting time for distinguishing a P3 component from an event-related potential after highlighting. As a result, an electroencephalogram interface having a good response and excellent manipulability can be realized because of an ability to operate immediately after highlighting.

Hereinafter, the electroencephalogram interface system according to the present embodiment will be described.

Figure 12:
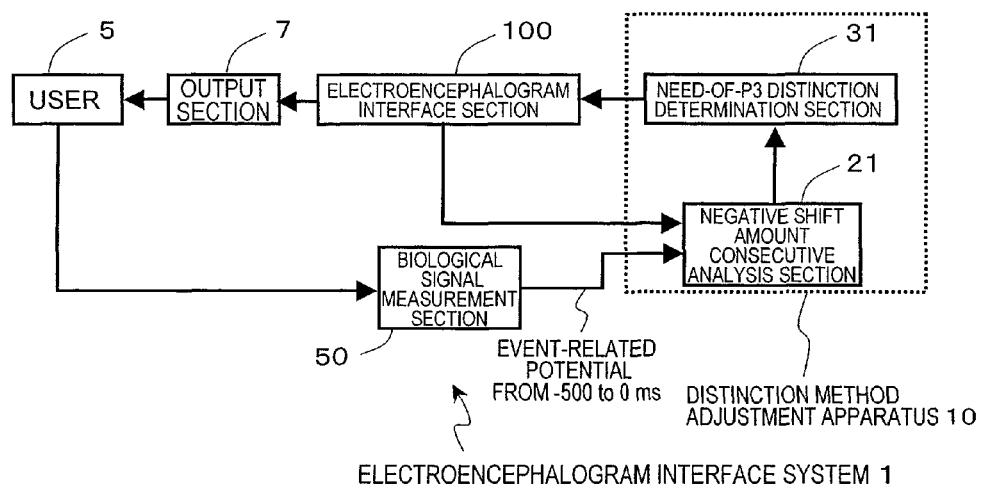
FIG. 12 A diagram showing a functional block construction of the electroencephalogram interface system 1 according to an embodiment of the present invention.

FIG. 12 shows a functional block construction of the electroencephalogram interface system 1 according to the present embodiment. The electroencephalogram interface system 1 includes an output section 7, a distinction method adjustment apparatus 10, a biological signal measurement section 50, and an electroencephalogram interface (IF) section 100. FIG. 12 also shows detailed functional blocks of the adjustment apparatus 10. The user 5 block is illustrated for convenience of explanation. The output section 7 presents a screen on which a menu and the like are presented to the user 5.

The user 5 is merely carefully looking, as to whether a menu item concerning a device manipulation which is presented by the electroencephalogram interface section 100 on the output section 7 is highlighted or not, and does not make any manipulation input. However, the device operates in accordance with the menu item which is selected via the electroencephalogram interface section 100.

The distinction method adjustment apparatus 10 is connected to the biological signal measurement section 50 and the electroencephalogram interface section 100 in a wireless or wired manner, and performs transmission and reception of signals. Although FIG. 12 illustrates the biological signal measurement section 50 and the electroencephalogram interface section 100 as separate entities from the distinction method adjustment apparatus 10, this is only exemplary. A part or whole of the biological signal measurement section 50 and the electroencephalogram interface section 100 may be provided within the distinction method adjustment apparatus 10, or implemented as a single device.

The biological signal measurement section 50 is an electroencephalograph which detects a biological signal of the user 5, and measures an electroencephalogram as a biological signal. The electroencephalograph may a head-mounted electroencephalograph as shown in FIG. 1. It is assumed that the user 5 has put on the electroencephalograph in advance.

Electrodes are disposed on the biological signal measurement section 50 so that, when worn on the head of the user 5, the electrodes come into contact with the head at predetermined positions. The positioning of the electrodes may be, for example, Pz (median parietal), A1 (earlobe), and the nasion of the user 5. However, it will suffice if there are at least two electrodes, and potential measurement will be possible with only Pz and A1, for example. These electrode positions are to be determined based on reliability of signal measurements, wearing ease, and the like.

Thus, the biological signal measurement section 50 is able to measure the event-related potential of the user 5. The measured electroencephalogram of the user 5 is sampled so as to be computer-processible, and are sent to the electroencephalogram interface section 100 and the distinction method adjustment apparatus 10. Note that, in order to reduce the influence of noises which may be mixed in the electroencephalogram, the electroencephalogram to be measured in the biological signal measurement section 50 are subjected to band-pass filtering from e.g. 0.05 to 20 Hz in advance, and to baseline correction with respect to an average potential at e.g. 50 milliseconds before highlighting of menu items.

The electroencephalogram interface section 100 presents menu items concerning device manipulations to the user in random order, e.g., at an interval of 1 second, cuts out the electroencephalogram measured by the biological signal measurement section 50, and subjects it to distinction. Then, it controls the device operation according to the distinction result. The basic operation of the electroencephalogram interface section 100 is as described above.

Assuming that the device to be controlled by using the electroencephalogram interface section 100 is the TV 2 shown in FIG. 1, for example, the menu is visually presented to the user 5 via the output section 7.

From the electroencephalogram of the user 5 after highlighting of a menu item as measured by the biological signal measurement section 50, the electroencephalogram interface section 100 cuts out e.g. 500 ms since the point of highlighting the menu item as a starting point, which is longer than the peak latent period of the P3 component, and distinguishes the waveform. The time for which to cut out the electroencephalogram may be 1000 ms in order to account for a return from a peak of the waveform. The method of distinguishing the event-related potential may be to simply subject the waveform to threshold value processing, or as described in Japanese Laid-Open Patent Publication No. 10-146323, a correlation coefficient may be determined with respect to a template which is generated from an arithmetic mean waveform of the P3 component that has been measured with respect to each user in advance. Parameters for the distinction are adjusted by the distinction method adjustment apparatus 10 according to a method described later.

Next, the detailed construction of the distinction method adjustment apparatus 10 according to the present embodiment will be described. One main feature of the present invention lies in the construction and operation of the distinction adjustment apparatus 10.

The distinction method adjustment apparatus 10 includes a negative shift amount consecutive analysis section 21 and a need-of-P3 distinction determination section 31.

From the electroencephalogram interface section 100, the negative shift amount consecutive analysis section 21 acquires information indicating an interval of highlighting the menu items. Moreover, the negative shift amount consecutive analysis section 21 receives information of an electroencephalogram signal (or more specifically, event-related potential) of the user 5 as measured by the biological signal measurement section 50 in a time slot which is before highlighting of a menu item and which receives little influence from the highlighting of a previous menu item, cuts out the waveform of the event-related potential, and determines a gradient of the waveform.

Herein, the "time slot which receives little influence" is to be understood as follows: for example, assuming that the interval of highlighting the menu items is 1 second (1000 ms) and the reference point at which highlight occurs is 0 ms, the negative shift amount consecutive analysis section 21 cuts out the waveform of an event-related potential from −600 ms to 0 ms. Then, the negative shift amount consecutive analysis section 21 further passes it through a 2 Hz low-pass filter, and thereafter determines the gradient of the waveform. It is assumed that the negative shift amount consecutive analysis section 21 retains this value of "600 ms" as an offset value for specifying a point of time at which to start a cut-out, retrospectively from the reference point. It will be appreciated that this value is shorter than the highlighting interval t of the menu items. Note that the negative shift amount consecutive analysis section 21 may acquire information specifying such a highlighting interval t from the electroencephalogram interface section 100, and appropriately set an offset value (T) which is shorter than the highlighting interval based on that information. As a result, the negative shift amount consecutive analysis section 21 may cut out the waveform of an event-related potential from a point t2(=t1−T) (i.e. t2 is earlier than the point of highlight t1 by time T) until point t1, and then determine the gradient of the waveform by the least-squares method.

In order to determine the gradient of the waveform, the least-squares method is used, for example. The zone in which to cut out the waveform may be any time slot which receives little influence from highlighting of an immediately previous menu item, depending on the interval of highlighting the menu items. Note that the negative shift amount may be determined from one sample of waveform for each highlight, or may be determined from a waveform which is obtained by taking an arithmetic mean of the waveforms of the highlights up to then.

The need-of-P3 distinction determination section 31 determines whether the gradient of the waveform received from the negative shift amount consecutive analysis section 21 is smaller than a threshold value or not, for example, and determines whether or not a P3 component distinction needs to be performed in the electroencephalogram interface section 100. The threshold value may be determined for each user, or previously set, e.g. −5 µV/s.

In the present embodiment, it is determined whether the user was issuing an electroencephalogram for making a menu selection or not based only on the negative shift amounts at menu presentation, and a selected item is determined. When the gradient of the waveform before a certain highlight is smaller than the threshold value, the need-of-P3 distinction determination section 31 determines that the highlight was directed to the selected item, and an adjustment is made so that P3 component distinction is not performed in the electroencephalogram interface section 100. For example, the need-of-P3 distinction determination section 31 instructs the electroencephalogram interface section 100 not to perform a P3 component distinction. At the same time, the need-of-P3 distinction determination section 31 instructs the electroencephalogram interface section 100 to operate a device based on the result of determination that the highlight was directed to the selected item.

On the other hand, if the gradient of the waveform is equal to or greater than the threshold value, the need-of-P3 distinction determination section 31 does not perform anything, and a P3 component distinction is performed in the electroencephalogram interface section 100. Based on an event-related potential from the biological signal measurement section 50 within a predetermined period (e.g., 0 to 500 ms) from highlighting of each menu item, the electroencephalogram interface section 100 identifies the selected menu item.

With this construction, based on negative shift amounts before highlighting, it becomes possible to determine whether or not a P3 component distinction needs to be performed in the electroencephalogram interface section 100 with respect to an event-related potential after highlighting. As a result, when a negative shift amount before highlighting is smaller than a threshold value, it becomes possible to determine a menu item meant to be selected before highlighting, thus eliminating the waiting time for performing a P3 component distinction from an event-related potential after highlighting. Thus, there is realized an electroencephalogram interface having a good response and excellent manipulability.

With this construction, a menu item which the user was wishing to select can be determined based on the negative shift amount of an electroencephalograms before highlighting as an index. As a result, device operations which are not intended by the user are reduced, whereby an electroencephalogram interface which is easy for the user to use can be realized. Moreover, presence or absence of a menu item which the user was wishing to select can be predicted with one cycle of menu item highlights, thus enabling rapid processing.

Next, with reference to a flowchart of FIG. 13, an overall procedure of processing performed by the electroencephalogram interface system 1 will be described.

Figure 13:
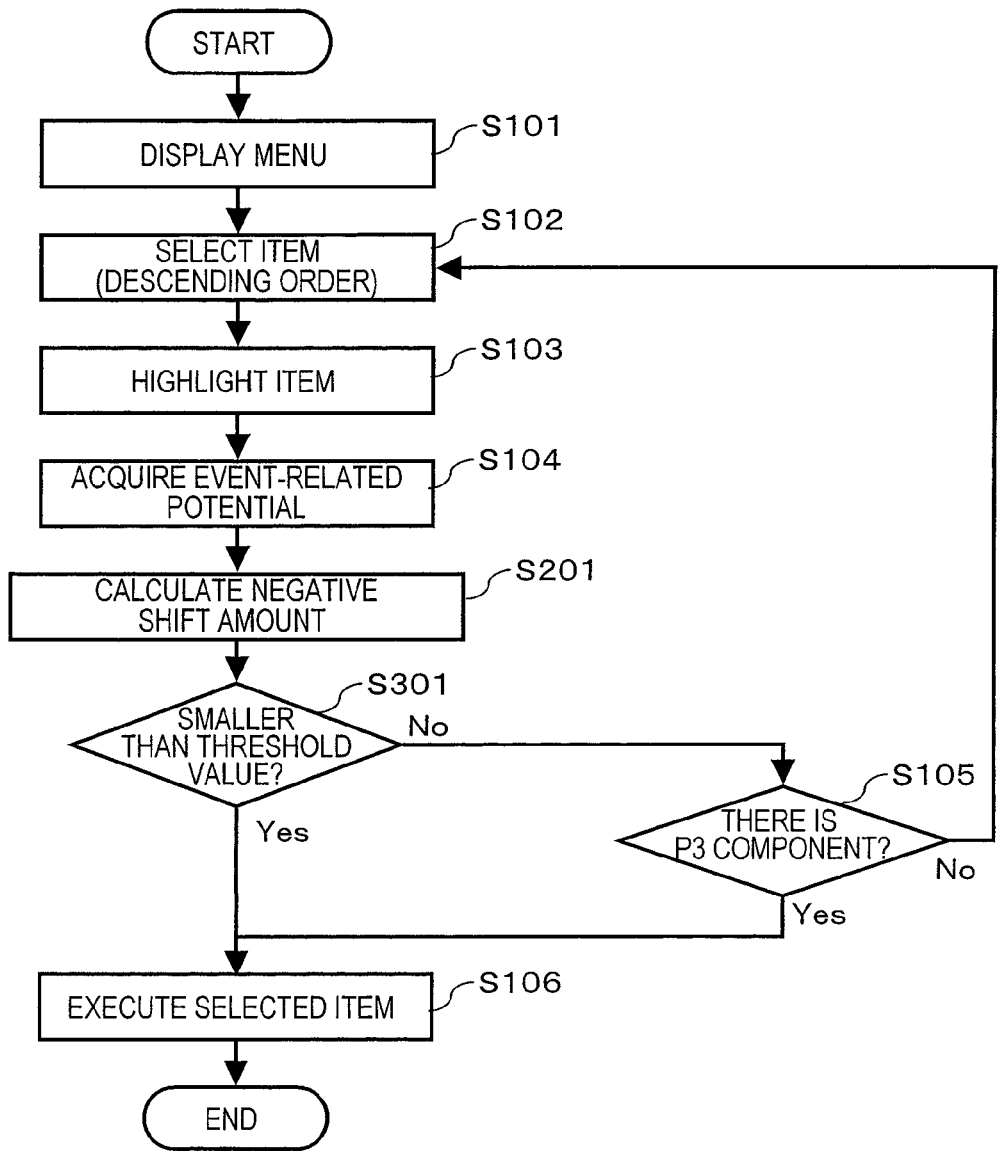
FIG. 13 A flowchart showing a processing procedure by the electroencephalogram interface system 1 according to an embodiment of the present invention.

FIG. 13 shows a processing procedure by the electroencephalogram interface system 1 according to the present embodiment. Note that step S101 to step S106 shown in FIG. 13 are identical to the processing procedure by the electroencephalogram interface shown in FIG. 3. Therefore, the descriptions thereof will be omitted below. However, it is assumed that the item selection at step S102 is performed in descending order.

At step S201, from the electroencephalogram measured by the biological signal measurement section 50 at step S104, the negative shift amount consecutive analysis section 21 cuts out an electroencephalogram before highlighting, and after passing it through a low-pass filter, consecutively determines a gradient of the waveform for each highlight. The time period for which the electroencephalogram is cut out may be about a half of the interval with which one cycle of menu item highlighting is completed. The low-pass filter may be set to e.g. 2 Hz, according to the time over which the cut-out is made. In order to determine the gradient of each waveform, the least-squares method is used, for example.

The next step S301 is a branching based on a result of comparison by the need-of-P3 distinction determination section 31 between a prestored threshold value and the gradient of the waveform before highlighting of a menu item as consecutively determined by the negative shift amount consecutive analysis section 21 at step S201.

If the gradient of the waveform is smaller than the threshold value (Yes at step S301), it is determined that the user has selected that menu item, and an adjustment is made so that P3 component distinction is not performed in the electroencephalogram interface section 100, and control proceeds to step S106 to execute the determined menu item.

On the other hand, if the gradient of the waveform is equal to or greater than the threshold value (No at step S301), the need-of-P3 distinction determination section 31 does not perform anything, and control proceeds to step S105, where a P3 component distinction is performed by the electroencephalogram interface section 100. Note that, since the selected item is to be determined based only on the negative shift amount, the threshold value at step S301 may be chosen more stringently than the threshold value of step S201.

Through such processing, menu items are highlighted in descending order; the negative shift amount of an electroencephalogram before highlighting is consecutively determined for each highlight; and an adjustment as to the need to perform a P3 component distinction in the electroencephalogram interface section 100 can be made based on the negative shift amounts.

Figure 14:
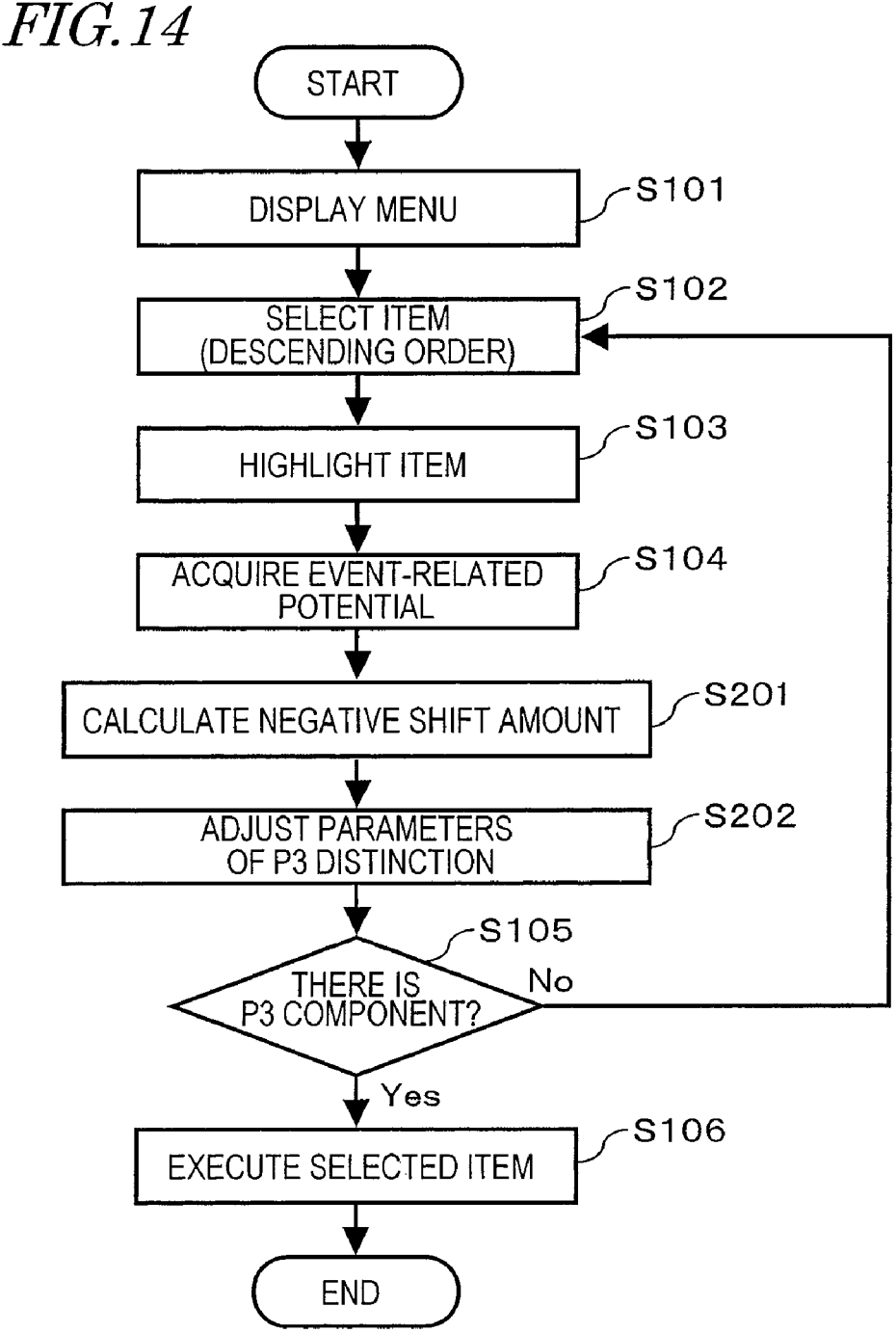
FIG. 14 A flowchart showing a processing procedure by the electroencephalogram interface system 1.

Note that a processing which combines the processing of the present embodiment as shown in FIG. 13 and the processing as shown in FIG. 14 is also possible. For example, in the distinction method adjustment apparatus 10, threshold value a and threshold value b (where threshold value a>threshold value b) may be stored, and the event-related potential waveform before a certain highlight may be compared against gradient x, and the following processing is possible: if (1) threshold value b>gradient x, that highlight is determined as the selected item and P3 distinction is not performed, as in the process of FIG. 13; (2) if threshold value a>gradient x>threshold value b, the process of FIG. 14 is performed to adjust parameters of P3 distinction; and if (3) threshold value a<gradient x, nothing is performed.

Note that all steps in FIG. 14 except for step S202 are as have already been described in connection with FIG. 3 and FIG. 13. At step S202, the need-of-P3 distinction determination section 31 makes a comparison between a prestored threshold value and the gradient of the waveform before highlighting of each menu item as consecutively determined by the negative shift amount consecutive analysis section 21 at step S201, and depending on whether it is smaller than the threshold value or not, adjusts the distinction parameters of the electroencephalogram interface section 100. If the gradient of the waveform is smaller than the threshold value, a change is made such as decreasing the threshold value for P3 component distinction, so as to lean toward determining that the P3 component is contained after highlighting. Conversely, if the gradient of the waveform is equal to or greater than the threshold value, a change is made such as increasing the threshold value for P3 component distinction, so as to lean toward determining that the P3 component is not contained.

By providing the distinction method adjustment apparatus 10 in the electroencephalogram interface system 1 of the present embodiment, menu items are highlighted in descending order; the gradient of an event-related potential before highlighting (negative shift amount) is consecutively determined for each highlight; and if the gradient of the waveform is smaller than a threshold value, the distinction method is adjusted so that P3 component distinction is not performed in the electroencephalogram interface section 100. Thus, when the negative shift amount before highlighting is smaller than the threshold value, it becomes possible to determine a menu item meant to be selected before highlighting, thus eliminating the waiting time for performing a P3 component distinction from an event-related potential after highlighting. Thus, there is realized an electroencephalogram interface having a good response and excellent manipulability.

In the above-described embodiment, when the negative shift amount is smaller than the threshold value (Yes from step S301 in FIG. 13), it is determined that the user has selected that menu item, and an adjustment is made so that P3 component distinction in the electroencephalogram interface section 100 is not performed. However, in that case, prospects of the menu item which the user wishes to select may be narrowed down on the basis of the event-related potentials before highlighting, and thereafter a P3 component distinction may be performed in the electroencephalogram interface section 100, and it may be determined whether the result of distinction is included among the prospects or not. This is considered to provide for an increased accuracy.

In the above-described embodiment, menu item highlights are arranged in the vertical direction (e.g. FIG. 6), such that each menu item is highlighted in descending order from top to bottom; however, this is only an example. It should be clear to those skilled in the art that, in any situation where the user is able to predict which menu item will be next highlighted based on the positioning of menu items and the order of highlighting, an event-related potential as shown in FIG. 11 will be obtained. Therefore, the menu selection process according to the present invention is also possible in the following cases: where obliquely-arranged menu items are sequentially highlighted in a certain direction; where highlighting is performed in ascending order (from bottom to top); and highlighting is performed in an order which has been learned by the user (e.g., every other item, or in the order of frequency of use), for example.

Regarding the above-described embodiment, too, the processes which have been described with reference to flowcharts can be implemented as a program which is executed by a computer. Such a computer program is distributed on the market in the form of a product recorded on a storage medium such as a CD-ROM, or transmitted through telecommunication lines such as the Internet. All or some of the constituent elements composing the distinction method adjustment apparatus and the electroencephalogram interface section may be implemented as a general-purpose processor (semiconductor circuit) executing a computer program. Alternatively, they may be implemented as a special processor in which such a computer program and a processor are integrated.

With a distinction method adjustment apparatus according to the present invention and an electroencephalogram interface system in which the distinction method adjustment apparatus is incorporated, it is possible to detect when a user who is manipulating an electroencephalogram interface is not issuing an electroencephalogram for making a menu selection, based on the negative shift amount of an electroencephalogram of the user before highlighting. Since there is no need to add a gaze detection apparatus or the like, it is possible to reduce cost and reduce the scale of the system.

In accordance with the distinction method adjustment apparatus and the electroencephalogram interface system, based on an electroencephalogram before a menu item is highlighted (especially event-related potential), it is possible to determine which menu item a user was wishing to select. As a result, rapid processing is expectable, and a reduction in the device operations which are not intended by the user can be realized. For example, in the case where a wearable device (head-mount display or music player) is manipulated with an electroencephalogram interface, it is presumable that noises originating from myoelectric potential, electro-oculographic potential, or commercial power may be mixed, thus making the distinction of an electroencephalogram difficult. However, when the distinction method adjustment apparatus according to the present invention is applied, an electroencephalogram interface which is not very susceptible to noise influences can be realized. Since such functions of a distinction method adjustment apparatus can be realized by a computer program, for example, an easy implementation is possible without significant modifications of the system.

While the present invention has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the invention that fall within the true spirit and scope of the invention.

What is claimed is:

1. An adjustment apparatus for use in an electroencephalogram interface system, the electroencephalogram interface system having:
   an output section for visually presenting a manipulation menu for a device,
   a biological signal measurement section for acquiring an electroencephalogram signal from a user, and
   an electroencephalogram interface section for presenting via the output section a plurality of menu items of the manipulation menu in a regular order, distinguishing by a previously determined distinction method a component of an event-related potential which is contained in the electroencephalogram signal after each menu item is highlighted, and operating the device based on the distinguished event-related potential,
   the adjustment apparatus adjusting the distinction method in the electroencephalogram interface section, wherein the distinction method is a method of distinguishing the component of the event-related potential depending on whether the electroencephalogram signal satisfies a predetermined criterion or not,
   the adjustment apparatus for the electroencephalogram distinction method comprising:
   an analysis section for determining a gradient of a waveform of the event-related potential before the menu item is highlighted; and
   a determination section for comparing the gradient of the waveform as determined by the analysis section against a threshold value, and determining that the menu item corresponding to the gradient is a menu item which the user wishes to select based on a result of comparison.

2. The adjustment apparatus of claim 1, wherein, if the gradient of the waveform determined by the analysis section is smaller than a predetermined negative threshold value, the determination section determines that the menu item corresponding to the gradient is the menu item which the user wishes to select, and instructs the electroencephalogram interface section to operate the device based on the result of determination.

3. The adjustment apparatus of claim 1, wherein, when determining that the menu item corresponding to the gradient is the menu item which the user wishes to select, the determination section instructs the electroencephalogram interface section not to perform distinction of the component of the event-related potential which is contained in the electroencephalogram signal after the menu item is highlighted.

4. The adjustment apparatus of claim 2, wherein the determination section obtains the gradient of the waveform by dividing the event-related potential ($\mu V$) by time (s), and compares the gradient against the negative threshold value, the negative threshold value being $-4$.

5. The adjustment apparatus of claim 2, wherein,
   if the gradient of the waveform determined by the analysis section is greater than the predetermined negative threshold value, the determination section does not give any instruction to the electroencephalogram interface section; and
   the electroencephalogram interface section distinguishes the component of the event-related potential which is contained in the electroencephalogram signal after each menu item is highlighted.

6. The adjustment apparatus of claim 2, wherein,
   the analysis section acquires information t representing a time interval of highlighting from the electroencephalogram interface section, and cuts out a waveform of the event-related potential from point t2 until point t1, such that point t1 is a point where the menu item is highlighted and point t2 is earlier than point t1 by a predetermined time.

7. The adjustment apparatus of claim 6, wherein the analysis section employs a least-squares method to determine the gradient of the waveform of the event-related potential having been cut out.

8. A method used for adjusting a distinction method in an electroencephalogram interface system, the electroencephalogram interface system having:
   an output section for visually presenting a manipulation menu for a device,
   a biological signal measurement section for acquiring an electroencephalogram signal from a user, and
   an electroencephalogram interface section for presenting via the output section a plurality of menu items of the manipulation menu in a regular order, distinguishing by a previously determined distinction method a component of an event-related potential which is contained in the electroencephalogram signal after each menu item is highlighted, and operating the device based on the distinguished event-related potential, the adjustment method adjusting the distinction method in the electroencephalogram interface section, wherein the distinction method is a method of distinguishing the component of the event-related potential depending on whether the electroencephalogram signal satisfies a predetermined criterion or not, the adjustment method comprising the steps of:

determining a gradient of a waveform of the event-related potential before the menu item is highlighted; and comparing the gradient of the waveform as determined by the step of determining a gradient against a threshold value, and determining that the menu item corresponding to the gradient is a menu item which the user wishes to select based on a result of comparison.

9. A non-transitory computer readable medium storing executable code in an electroencephalogram interface system, the electroencephalogram interface system having:

an output section for visually presenting a manipulation menu for a device, a biological signal measurement section for acquiring an electroencephalogram signal from a user, and an electroencephalogram interface section for presenting via the output section a plurality of menu items of the manipulation menu in a regular order, distinguishing by a previously determined distinction method a component of an event-related potential which is contained in the electroencephalogram signal after each menu item is highlighted, and operating the device based on the distinguished event-related potential, the executable code when executed adjusting the distinction method in the electroencephalogram interface section, wherein the distinction method is a method of distinguishing the component of the event-related potential depending on whether the electroencephalogram signal satisfies a predetermined criterion or not, the executable code when executed causing the electroencephalogram interface system to execute the steps of:

determining a gradient of a waveform of the event-related potential before the menu item is highlighted; and comparing the gradient of the waveform as determined by the step of determining a gradient against a threshold value, and determining that the menu item corresponding to the gradient is a menu item which the user wishes to select based on a result of comparison.

* * * * *